United States Patent [19]

Sasaki

[11] Patent Number: 4,559,840
[45] Date of Patent: Dec. 24, 1985

[54] LIFTING APPARATUS

[75] Inventor: Toshihiko Sasaki, Hyogo, Japan

[73] Assignee: Mitsubishi Denki Kabushiki Kaisha, Tokyo, Japan

[21] Appl. No.: 466,353

[22] PCT Filed: Jun. 10, 1982

[86] PCT No.: PCT/JP82/00224

§ 371 Date: Feb. 14, 1983

§ 102(e) Date: Feb. 14, 1983

[30] Foreign Application Priority Data

Jun. 12, 1981 [JP] Japan .................. 56-87547[U]

[51] Int. Cl.[4] .................. F16H 19/06; B66B 7/04
[52] U.S. Cl. .................. 74/89.21; 74/425; 187/9 R
[58] Field of Search .................. 74/89.21, 37, 10.7, 74/505, 425; 187/9 R, 20

[56] References Cited

U.S. PATENT DOCUMENTS

| | | | |
|---|---|---|---|
| 876,730 | 1/1908 | Rushe | 74/505 |
| 1,249,931 | 12/1917 | Eller et al. | 74/44 |
| 1,594,513 | 8/1926 | Ainsworth | 74/89.21 |
| 2,565,401 | 8/1951 | Smith | 74/25 X |
| 2,860,871 | 11/1958 | Schneider | 74/89.21 |
| 3,390,815 | 7/1968 | Kavan et al. | 222/333 X |
| 4,222,461 | 9/1980 | Gunti | 187/20 |
| 4,358,239 | 11/1982 | Dechantsreiter | 74/89.21 X |

FOREIGN PATENT DOCUMENTS

EP21808 1/1981 European Pat. Off. .......... 187/9 R

Primary Examiner—Allan D. Herrmann
Attorney, Agent, or Firm—Oblon, Fisher, Spivak, McClelland & Maier

[57] ABSTRACT

The disclosure describes a lifting apparatus used to raise and lower a device such as a water quality detector installed outdoor. It comprises a cylindrical body in which main elements are contained, a slit formed in the cylindrical body along the axial direction, a movable body having a guide plate which is fitted into the slit and is connected with both ends of a chain, the chain being wound between a sprocket placed at the upper inner portion of the cylindrical body and the sprocket of a driving means so as to be driven to raise or lower to guide plate and the movable body connected to the guide plate.

2 Claims, 11 Drawing Figures

FIGURE 1 *PRIOR ART*

FIGURE 7
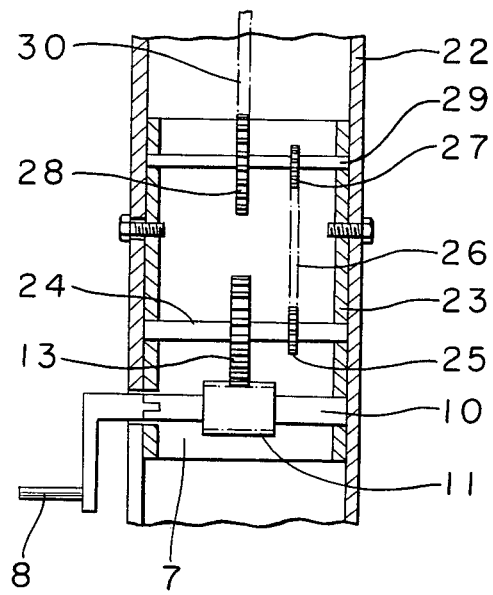
FIGURE 9
FIGURE 8
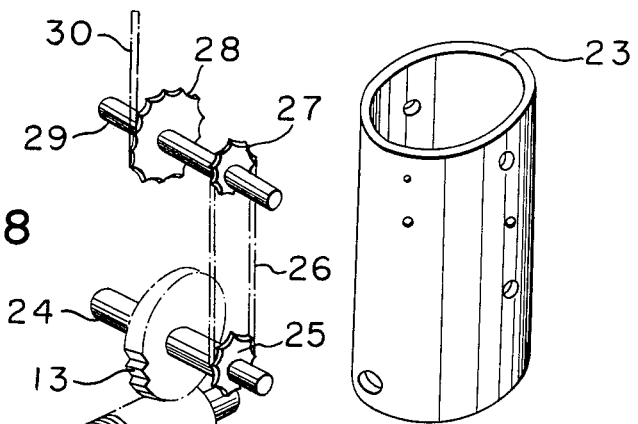
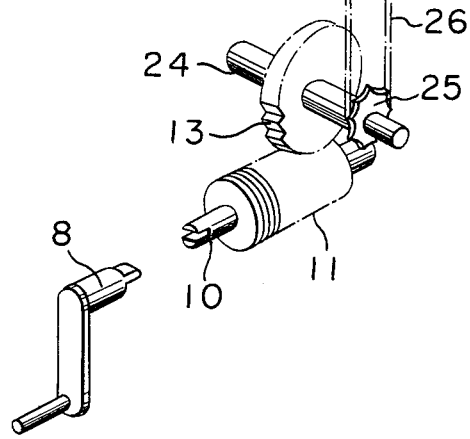

LIFTING APPARATUS

FIELD OF TECHNOLOGY

The present invention relates to a lifting apparatus and more particularly relates to a lifting apparatus useful for application to the elevator of an outdoor water quality detector installed.

BACKGROUND OF TECHNOLOGY

FIGS. 1 to 3 show a prior art apparatus of this kind. In the figures, the reference numeral (1) designates water to be tested, (2) a water quality detector, (3) a base, (4) a moving wheel, (5) and (6) designate supporters, (7) designates a container for containing a winding device, (8) a handle for raising and lowering operation, (9) a fitting plate, (10) a worm shaft, (11) a worm secured to the worm shaft (10), (12) a winding shaft, (13) a worm wheel and (14) a winding drum which is fixed together with the worm wheel to the winding shaft. The reference numeral (15) designates a wire having one end secured to the drum to control the raising and lowering of the water quality detector (2). The reference numeral (16) designates a pulley, (17) a guide roller, (18) a guide roller shaft, (19) a movable frame, (2) a water quality detector supporting arm, and (21) a bracket for holding the detector (2).

A description will now be made be made of the operation of the apparatus. In raising and lowering, the worm (10) and the worm wheel (11) in the container (7) are rotated by the revolution of the handle (8) with the consequence that the winding drum (14) is rotated through the worm wheel meshed with the worm (11). since this revolution causes the wire (15) to be wound, the movable frame (19) connected to one end of the wire (15) is vertically moved by the aid of the roller shafts (18) and the guide rollers (17) mounted on the movable frame and the supporters (5), (6). Thus, the water quality detector (2) is vertically moved through the bracket (21) and the water quality detector supporting arm (20) fixed to the movable frame (19).

In the conventional lifting apparatus described above, a winding drum for winding the wire has been needed and furthermore, when the apparatus is a substantial height, it has been necessary to use a large drum and movable frame. When the water quality detector is lowered by rewinding the drum (14) to loosen the wire (15) so that the deadweights of the water quality detector (2) and the movable frame (19) pulls them down, a smooth lowering operation can not be attained due to the small load and the frictional resistance of the sliding parts. Additionally, it has been disadvantageous in that it is difficult to conceal the container for containing the winding device and the movable frame guide rollers from the atmosphere and two supporters are needed thereby resulting a large apparatus.

DISCLOSURE OF THE INVENTION

The present invention provides a structure in which a lifting mechanism is contained in a cylindrical shaft and combination of a chain and a chain sprocket wheel is used. With this structure, a lifting apparatus having a single cylindrical shaft can be realized to provide reliable raising and lowering operation. In addition, the single cylindrical shaft as a supporter makes concealment of winding device from the atmosphere easy and provide an apparatus of compact, light weight, economical and beautiful in appearance.

BRIEF DESCRIPTION OF DRAWINGS

FIGS. 1 to 3 show the conventional lifting apparatus for a water quality detector, wherein FIG. 1 is a side view partly sectioned, FIG. 2 a front view partly sectioned and FIG. 3 is a sectional view taken along the line III—III of FIG. 2.

FIGS. 4 to 11 show a single cylindrical shaft type water quality detector rotary transferring lifting apparatus wherein FIG. 4 is a sectional side view showing a lifting mechanism held in the single single cylindrical shaft, FIG. 5 is a partly enlarged sectional view of sliding parts for raising and lowering operation, FIG. 6 is a sectional view taken along the line VI—VI of FIG. 5, FIG. 7 is an enlarged sectional view of a driving part for raising and lowering operation, FIG. 8 is a perspective view of the driving part, FIG. 9 is a perspective view of a casing for the driving part, FIG. 10 is an enlarged sectional view of an upper rotary transferring part of the single cylindrical shaft, and FIG. 11 is a perspective view of the upper rotary transferring part.

PREFERRED EMBODIMENT OF THE INVENTION

Figure 1:
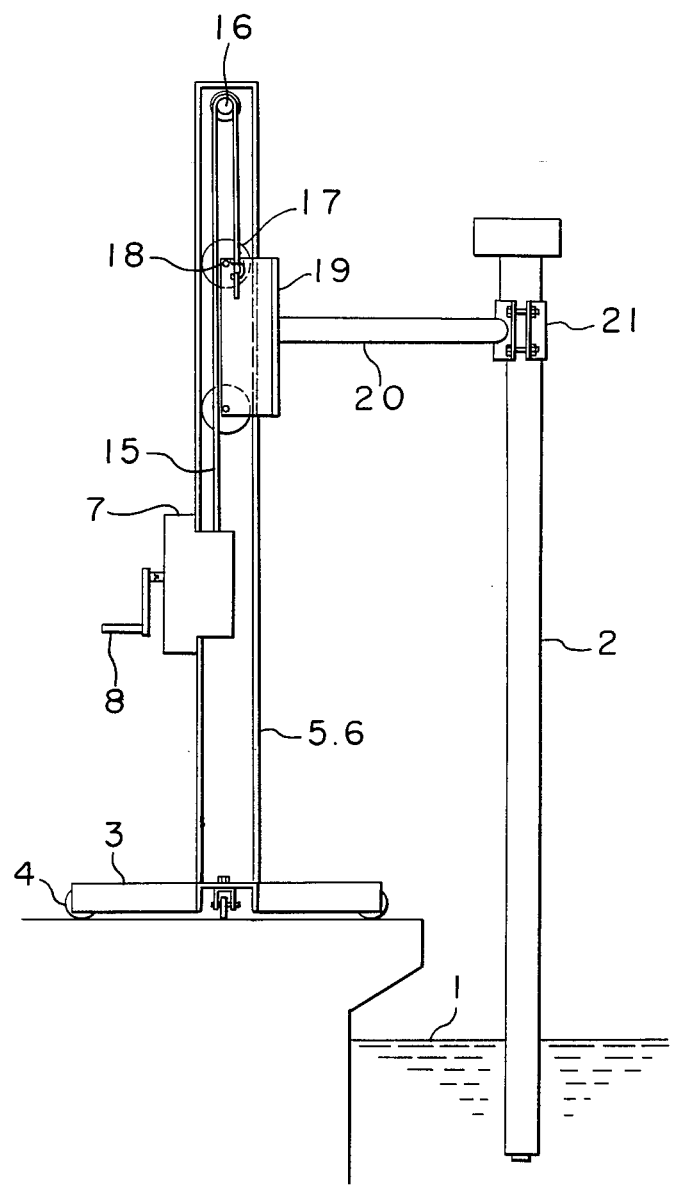
Figure 2:
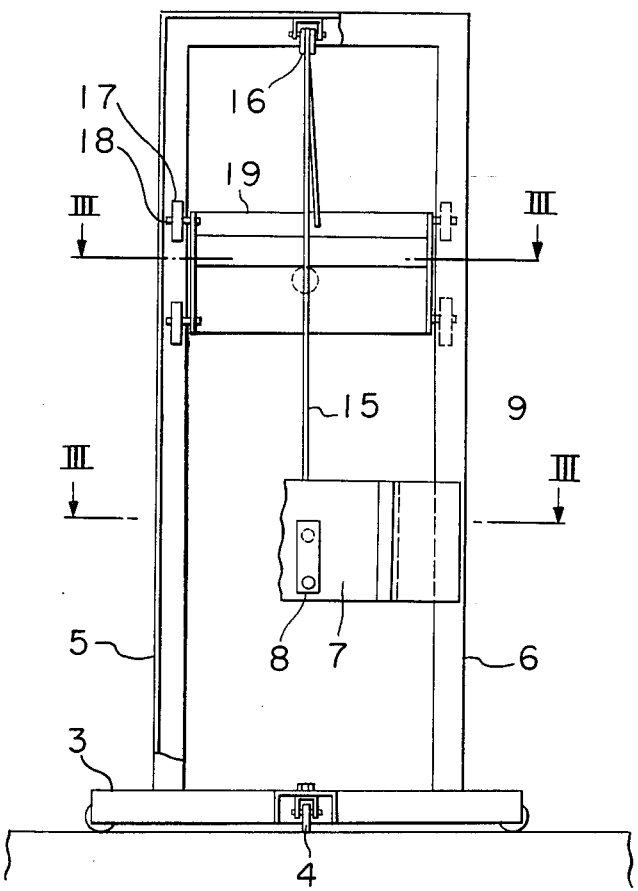
Figure 3:
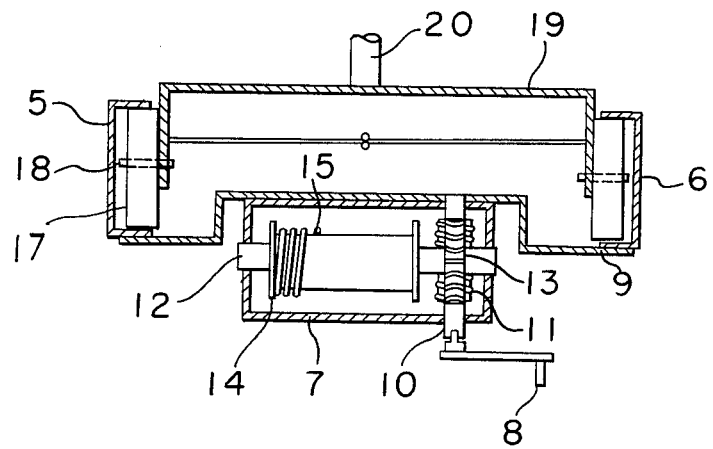
Figure 4:
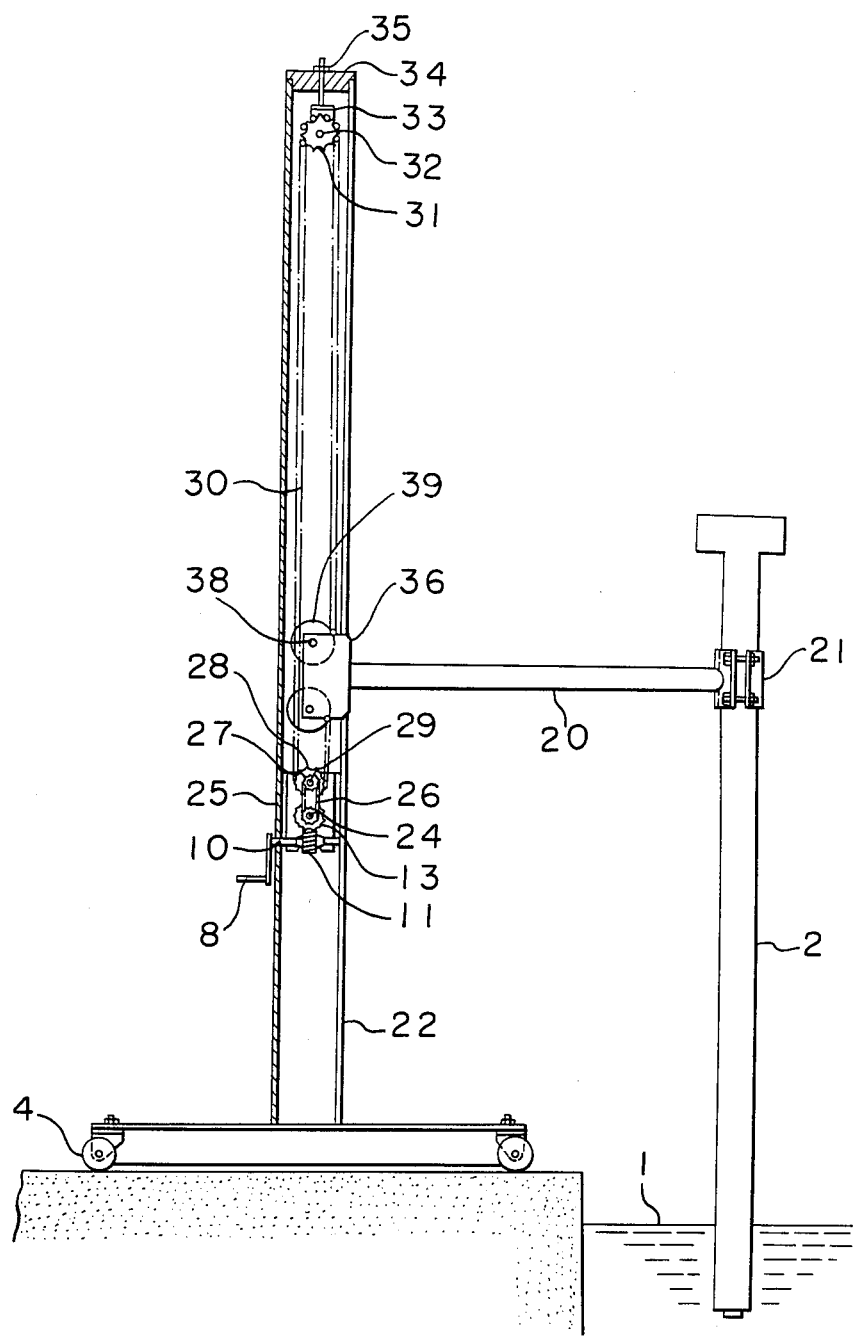
Figure 5:
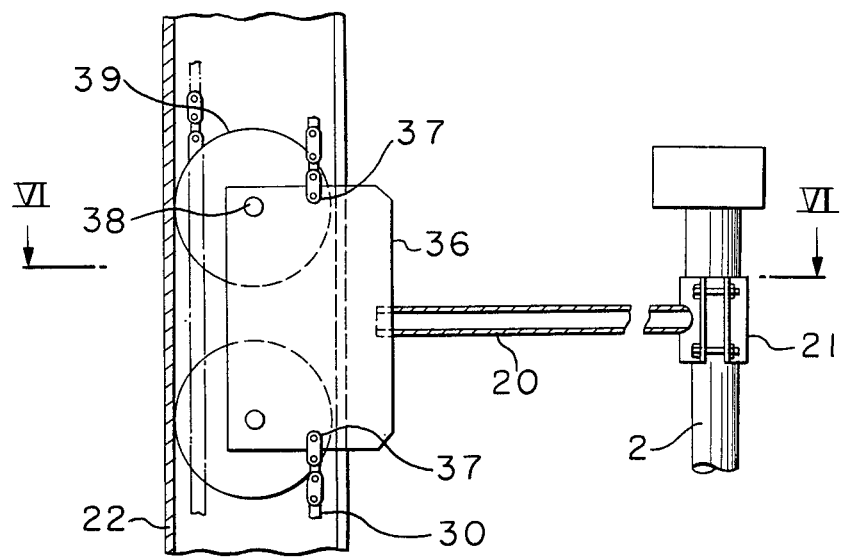
Figure 6:
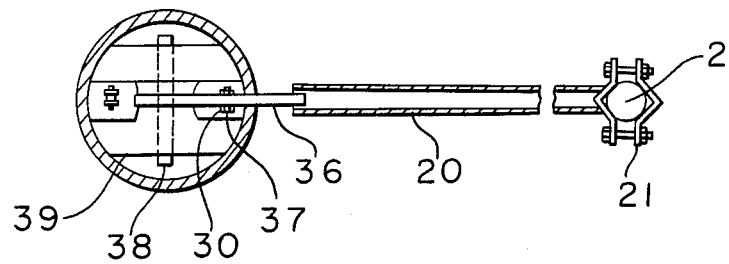
Figure 10:
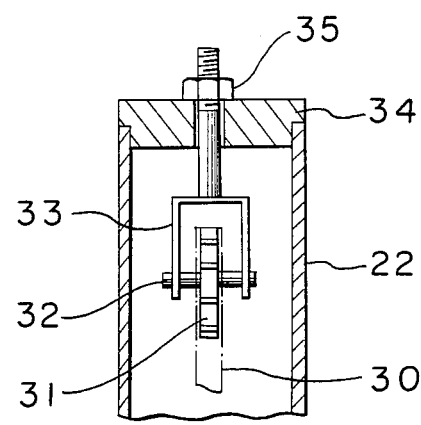
Figure 11:
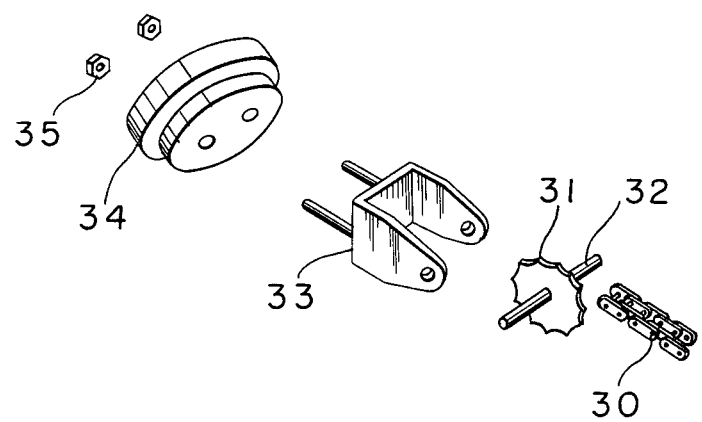

In FIGS. 4 to 11, the reference numeral (22) designates a single cylindrical shaft for holding a lifting mechanism described below, (23) a casing for a driving means which contains the driving means described below and has a cylindrical shape so that it can be held in the single cylindrical shaft. The reference numeral (24) designates a shaft, and (25) a chain sprocket wheel which is fixed to the shaft (24) as well as the worm wheel (13) described above. Reference numeral (26) designates a chain, (27), (28) respectively designate chain sprocket wheels and (29) designates a shaft on which the chain sprocket wheels are fixed and which is rotated by receiving a driving force from the chain sprocket wheel (25) and the chain (26). Reference numeral (30) designates a chain used for raising and lowering operation, (31) a rotary transferring chain sprocket wheel and (32) a shaft which supports the chain sprocket wheel (31) so as to be rotatable. Reference numeral (33) designates a bracket, (34) a cap which closes the top of the single cylindrical shaft and holds the bracket (33). Reference numeral (35) designates a lock nut, (36) a guide plate and (37) a pair of fixed pins which connect both ends of the chain (30) to the upper and lower portions of the guide plate (36) respectively. Reference numeral (38) designates a pair of shafts and (39) a pair of rollers which are rotatably supported by the guide plate to control vertical movement in the single cylindrical shaft (22).

The operation of the apparatus will now be described. Raising and lowering of the water quality detector (2) is carried out by the revolution of the handle (8). That is, the revolution of the handle (8) rotates the shaft (10), hence the worm (11) fixed to the shaft (10) and the worm wheel (13) meshed with the worm (11), the shaft (24) fixed to the worm wheels (13) and the chain sprocket wheel (25) are rotated. The chain sprocket wheels (27), (28) fixed to the shaft (29) are rotated through the chain (26). Since the chain for raising and lowering operation (30) meshed with the chain sprocket wheel (28) is fixed to both the ends of the guide plate (36) through the chain sprocket wheel (31), the revolution of the chain sprocket wheel (28) raises or lowers the guide plate (36) in the single cylindrical shaft under guidance of the rollers (39). The water quality detector supporting arm (20) fixed to the guide plate (36) and the water quality detector (2) held by the arm are, therefore, raised or lowered dependent on the direction of the revolution of the handle.

In the embodiment, the description is made on a manual operation; however, a motor may be used. Although the worm and the worm wheel are exemplified as means for converting the direction of rotation as well as a reduction gear, it is possible to use the structure of combination of a bevel gear as the rotational direction converting means and a spur gear as the reduction gear. Furthermore, although the chain (26) is used as means for transmitting the rotation of the shaft of the chain sprocket wheel for raising and lowering operation, it is possible to use spur gears. The same effect as in the embodiment can be obtained by providing it on the worm wheel shaft (24).

I claim:

1. An apparatus for lifting a load comprising:
   a cylindrical hollow body having a slit formed in the wall of said body in an axial direction;
   a guide plate mounted for axial movement within said body and extending through said slit to support said load;
   a base for supporting said body in a vertical position;
   a first sprocket rotatably mounted within said body at the upper end thereof;
   a second sprocket rotatably mounted within said body at the lower end thereof;
   a first chain having both ends connected to opposite ends of said guide plate to form a loop, said loop being engaged with said first and second sprockets;
   driving means within said body engaged with said second sprocket for turning said second sprocket to drive said chain, causing said guide plate to move along said slit and lift said load wherein said driving means comprises a crank, a worm turned by said crank, a worm wheel driven by said worm, a third sprocket means coaxially mounted with and rotatable with said second sprocket, a fourth sprocket coaxial with and rotatable with said worm wheel, a second chain which is continuous to form a second loop with said second loop being engaged with said third sprocket and said fourth sprocket; and
   a cylindrically shaped casing mounted inside said cylindrical hollow body wherein said cylindrically shaped casing houses said driving means so that only said crank protrudes outside of said casing and said hollow body.

2. An apparatus according to claim 1, wherein at least one wheel is mounted on said guide plate inside said body so that said wheel rolls along the inside wall of said body.

* * * * *